United States Patent [19]

Folena-Wasserman et al.

[11] Patent Number: 5,252,216
[45] Date of Patent: Oct. 12, 1993

[54] PROTEIN PURIFICATION

[75] Inventors: Gail Folena-Wasserman, Richboro; John H. O'Grady, King of Prussia; Thomas M. Smith, Drexel Hill, all of Pa.; John Lifter, Wellesley, Mass.

[73] Assignee: SmithKline Beecham Corporation, Philadelphia, Pa.

[21] Appl. No.: 857,022

[22] Filed: Mar. 24, 1992

[51] Int. Cl.$^5$ ............................................. B01D 15/08
[52] U.S. Cl. .................................. 210/635; 210/656; 530/380; 530/413; 530/416; 530/417; 530/420
[58] Field of Search ............ 210/635, 656, 659, 198.2; 530/380, 413, 416, 417, 420

[56] References Cited

U.S. PATENT DOCUMENTS

| | | | |
|---|---|---|---|
| 3,917,527 | 11/1975 | Shaltiel | 210/635 |
| 4,000,098 | 12/1976 | Hofstee | 210/690 |
| 4,508,833 | 4/1985 | Sonneborn | 210/672 |
| 4,743,680 | 5/1988 | Mathews | 530/413 |
| 4,765,903 | 8/1988 | D'Andrea | 210/635 |
| 4,770,781 | 9/1988 | Schmidt | 210/635 |
| 4,771,128 | 9/1988 | Ferris | 530/413 |
| 4,797,474 | 1/1989 | Patroni | 530/417 |
| 4,894,439 | 1/1990 | Dorin | 530/417 |
| 4,908,434 | 3/1990 | Mertelsmann | 530/413 |
| 4,920,196 | 4/1990 | Aggarwal | 530/417 |
| 4,981,799 | 1/1991 | Takahashi | 435/233 |
| 4,992,531 | 2/1991 | Patroni | 530/416 |
| 5,030,352 | 7/1991 | Varady | 210/502.1 |
| 5,159,063 | 10/1992 | Hammer | 530/380 |

Primary Examiner—Ernest G. Therkorn
Attorney, Agent, or Firm—Herbert H. Jervis; Edward T. Lentz; Stuart R. Suter

[57] ABSTRACT

This invention relates to the application of combination chromatography to the purification of complement receptor proteins.

49 Claims, No Drawings

PROTEIN PURIFICATION

FIELD OF THE INVENTION

This invention relates to the field of protein purification. More specifically, this invention relates to the application of combination chromatography to the purification of complement receptor proteins.

BACKGROUND OF THE INVENTION

Historically, protein purification schemes have been predicated on differences in the molecular properties of size, charge and solubility between the protein to be purified and undesired protein contaminants. Protocols based on these parameters include size exclusion chromatography, ion exchange chromatography, differential precipitation and the like.

Size exclusion chromatography, otherwise known as gel filtration or gel permeation chromatography, relies on the penetration of macromolecules in a mobile phase into the pores of stationary phase particles. Differential penetration is a function of the hydrodynamic volume of the particles. Accordingly, under ideal conditions the larger molecules are excluded from the interior of the particles while the smaller molecules are accessible to this volume and the order of elusion can be predicted by the size of the protein because a linear relationship exists between elusion volume and the log of the molecular weight. Size exclusion chromatographic supports based on cross-linked dextrans e.g. SEPHADEX ®, spherical agarose beads e.g. SEPHAROSE ® (both commercially available from Pharmacia AB. Uppsala, Sweden), based on cross-linked polyacrylamides e.g. BIO-GEL ® (commercially available from BioRad Laboratories, Richmond, Calif.) or based on ethylene glycol-methacrylate copolymer e.g. TOYOPEARL HW65S (commercially available from ToyoSoda Co., Tokyo, Japan) are useful in the practice of this invention.

Precipitation methods are predicated on the fact that in crude mixtures of proteins the solubilities of individual proteins are likely to vary widely. Although the solubility of a protein in an aqueous medium depends on a variety of factors, for purposes of this discussion it can be said generally that a protein will be soluble if its interaction with the solvent is stronger than its interaction with protein molecules of the same or similar kind. Without wishing to be bound by any particular mechanistic theory describing precipitation phenomena, it is nonetheless believed that the interaction between a protein and water molecules (occurs by hydrogen bonding with several types of uncharged groups and electrostatically as dipoles, with charged groups and that precipitants such as salts of monovalent cations (e.g. ammonium sulfate) compete with proteins for water molecules, thus at high salt concentrations, the proteins become "dehydrated" reducing their interaction with the aqueous environment and increasing the aggregation with like or similar proteins resulting in precipitation from the medium.

Ion exchange chromatography involves the interaction of charged functional groups in the sample with ionic functional groups of opposite charge on an adsorbent surface. Two general types of interaction are known. Anionic exchange chromatography mediated by negatively charged amino acid side chains (e.g. aspartic acid and glutamic acid) interacting with positively charged surfaces and cationic exchange chromatography mediated by positively charged amino acid residues (e.g. lysine and arginine) interacting with negatively charged surfaces.

More recently affinity chromatography and hydrophobic interaction chromatography techniques have been developed to supplement the more traditional size exclusion and ion exchange chromatographic protocols. Affinity chromatography relies on the interaction of the protein with an immobilized ligand. The ligand can be specific for the particular protein of interest in which case the ligand is a substrate, substrate analog, inhibitor or antibody. Alternatively, the ligand may be able to react with a number of proteins. Such general ligands as adenosine monophosphate, adenosine diphosphate, nicotine adenine dinucleotide or certain dyes may be employed to recover a particular class of proteins.

Hydrophobic interaction chromatography was first developed following the observation that proteins could be retained on affinity gels which comprised hydrocarbon spacer arms but lacked the affinity ligand. Although in this field the term hydrophobic chromatography is sometimes used, the term hydrophobic interaction chromatography(HIC) is preferred because it is the interaction between the solute and the gel that is hydrophobic not the chromatographic procedure. Hydrophobic interactions are strongest at high ionic strength, therefore, this form of separation is conveniently performed following salt precipitations or ion exchange procedures. Elusion from HIC supports can be effected by alterations in solvent, pH, ionic strength, or by the addition of chaotropic agents or organic modifiers, such as ethylene glycol. A description of the general principles of hydrophobic interaction chromatography can be found in U.S. Pat. No. 3,917,527 and in U.S. Pat. No. 4,000,098. The application of HIC to the purification of specific proteins is exemplified by reference to the following disclosures: human growth hormone (U.S. Pat. No. 4,332,717), toxin conjugates (U.S. Pat. No. 4,771,128), antihemolytic factor (U.S. Pat. No. 4,743,680), tumor necrosis factor (U.S. Pat. No. 4,894,439), interleukin-2 (U.S. Pat. No. 4,908,434), human lymphotoxin (U.S. Pat. No. 4,920,196) and lysozyme species (Fausnaugh, J. L. and F. E. Regnier, J. Chromatog. 359:131–146 (1986)).

This invention relates to the application of a combination of ion exchange, precipitation, HIC and size exclusion chromatography to the purification of complement receptor molecules and complement receptor-like molecules.

BRIEF DESCRIPTION OF THE INVENTION

This invention relates to a method for purifying a complement receptor protein from a mixture containing same comprising sequentially subjecting said mixture to a cationic chromatographic support, a hydrophobic interaction chromatographic support and a size exclusion chromatographic support and selectively eluting the protein from each support.

In another aspect the invention provides for the purification of a complement receptor protein from conditioned cell culture medium in which the protein containing medium is sequentially subjected to a) cationic exchange chromatography, b) ammonium sulfate precipitation c) hydrophobic interaction chromatography, d) anionic exchange chromatography, e) further cationic exchange chromatography, and f) size exclusion chromatography.

In another aspect this invention provides a method for purifying a complement receptor protein from a conditioned cell medium comprising:

(a) concentrating the conditioned cell medium;

(b) adsorbing the complement receptor protein onto a cationic exchange chromatographic column;

(c) washing the adsorbed protein with at least one buffer;

(d) eluting the washed protein;

(e) precipitating the protein with ammonium sulfate;

(f) resolubilizing the precipitated protein;

(g) adsorbing the protein from step (f) onto a hydrophobic interaction chromatographic support;

(h) selectively eluting the protein;

(i) adsorbing the eluate of step (h) onto an anionic exchange resin;

(j) eluting the adsorbed protein;

(k) adsorbing the eluate from step (j) onto a cationic exchange column;

(l) eluting the adsorbed protein;

(m) subjecting the eluate from step (l) to size exclusion chromatography and (n) recovering the protein therefrom.

DETAILED DESCRIPTION OF THE INVENTION

This invention relates to protein purification techniques which have application to the large scale purification of complement receptor proteins. The invention is particularly useful because it permits the recovery of receptor protein of >95% protein purity. The invention may be applied to the purification of a number of complement receptor proteins and complement receptor-like proteins.

Complement is a group of serum proteins, sequentially activated by limited proteolysis, that are important effectors of humoral immunity. Activation of complement occurs by interaction of early acting complement components with antigen/antibody complexes. Proteolytic fragments resulting from this activation alone or with other proteins activate additional complement proteins resulting in a proteolytic cascade reminiscent of the functioning of blood clotting factors. Alternatively, complement can be activated by bacterial cell wall components, proteolytic enzymes (e.g. plasmin) or complex carbohydrates (e.g. inulin). A number of biological activities are mediated by components of the complement system (e.g. immune cytolysis, anaphylatoxin production, bacteriolysis, chemotaxsis, hemolysis, opsonization, and phagocytosis).

Four classes of complement receptors (CR) are known (CR1–CR4). Complement receptor 1 (CR1) is a receptor for complement components C3b and C4b. Complement receptor 2 (CR2) is a receptor for component C3dg or C3d. Complement receptor 3 (CR3) is a receptor for C3bi. Complement receptor 4 (CR4) is a receptor for C3dg.

Complement receptor type 1 (CR1) is present on the membranes of erythrocytes, monocytes/macrophages, granulocytes, B cells, some T cells, splenic follicular dendritic cells, and glomerular podocytes. CR1 binds C3b and C4b and is referred to as the C3b/C4b receptor. Its primary sequence has been determined (Klickstein et al., J. Exp. Med. 165: 1095–1112 (1987), Klickstein et al.. J. Exp. Med. 168:1699–1717 (1988); Hourcade et al.. J. Exp. Med. 168:1255–1270 (1988)). It is composed of 30 short concensus repeats (SCRs) that contain 60–70 amino acids, of which 29 of the average 65 amino acids per SCR are conserved. It is proposed that each SCR forms a three dimensional triple loop structure through disulfide linkages with the third and first and the fourth and second half-cystines in disulfide bonds. The SCRs are further organized into 4 long homologous repeats (LHRs) of 7 SCRs each. Following a leader sequence, the molecule consists of the most N-terminal LHR-A comprising a C4b binding domain, the next two repeats, LHR-B and LHR-C comprising C3b binding domains, and the most C terminal LHR-D followed by 2 additional SCRs, a 25 residue putative transmembrane region and a 43 residue cytoplasmic tail.

CR1 is a member of a superfamily characterized by SCR homology. This superfamily contains members that also have a C3/C4 binding function, such as CR2, C4bp, factor H, factor B, and C2, as well as proteins without this function, such as interleukin-2 receptor, $\beta$2-glycoprotein I, Clr, haptoglobin $\alpha$ chain, and factor XIIIb.

CR1 is known to be a glycoprotein and its deduced amino acid sequence has 24 potential sites for N-linked oligosaccharides in the extracellular region. However, the synthesis of CR1 in the presence of tunicamycin (Lublin et al., J. Biol. Chem. 261: 5736 (1986)) and analysis of glucosamine content (Sim, Biochem J. 232: 883 (1985)) has suggested that only 6–8 of the available sites are actually linked to oligosaccharides. The N-terminus of the glycoprotein appears to be blocked.

Four different CR1 allotypes exist that differ in size by 30–50 kD increments. The gene frequencies of these allelic polymorphisms (allotypes) differ in the human population (Holer et al.. Proc. Natl. Acad. Sci. USA 84: 2459–2463 (1987)). The F (or A) allotype is composed of 4 LHRs and is about 250 kD; the larger S (or B) allotype contains a fifth LHR that is a chimera of the 5' half of LHR-B and the 3' half of LHR-A and is predicted to have a third C3b binding site (Wong et al., J. Exp. Med. 169: 847 (1989)), and is about 290 kD. The smallest F' (or C) allotype has increased incidence in patients with systemic lupus erythematosis (SLE) (Van Dyne et al., Clin. Exp. Immunol. 68:570 (1987) and Dykman et al., Proc. Natl. Acad Sci. USA 80: 1698 (1983)) and most likely arises from the deletion of LHR-B and one C3b binding site.

A naturally occurring soluble form of CR 1 and been detected in the plasma of normal individuals and certain individuals with SLE (Yoon & Fearon J. Immunol. 134: 3332-3338 (1985)). Its characteristics are similar to those of erythrocyte (cell-surface) CR1 both structurally and functionally.

Hourcade et al. (J. Exp. Med. 168: 1255–1270 (1988)) also observed an alternative polyadenylation site in the human CR1 transcriptional unit that was predicted to produce a secreted form of CR1. The mRNA that arises from this truncated sequence comprises the first 8.5 SCRs of CR1; e.g.,. the C4b binding domain, and could encode a protein of about 80 kD. When a cDNA corresponding to this truncated sequence was transfected into COS cells and expressed, it demonstrated the expected C4b, but not C3b binding activity (Kyrch et al., F.A.S.E.B J. 3:A368 (1989)). Krych et al. also observed a mRNA similar to the predicted one in several human cell lines and postulated that such a truncated soluble form of CR1 that is able to bind C4b may be synthesized in man.

Several soluble fragments of CR1 have also been generated via recombinant DNA procedures by eliminating the transmembrane region from the DNAs being expressed (Fearon et al., Intl. Patent Publication Number W089/09220, published Oct. 5, 1989 and Fearon et al. Intl. Patent Publication W091/05047 published Apr. 18, 1991). The soluble CR1fragments were functionally active, since they were able to bind C3b and/or C4b and demonstrate factor I cofactor activity depending upon the regions they contained. In addition they were able to act as inhibitors of in vitro CR1 functions such as neutrophil oxidative burst, complement mediated hemolysis, and C3a and C5a production. A soluble CR1construct, encoded by plasmid sCR1/pBSCR1c, also demonstrated in vivo activity in a reversed passive arthus reaction (Fearon et al. 1989 & 1991 and Yeh et al., J. Immunol (1991)) and suppressed post-ischemic myocardial inflammation and necrosis (Fearon et al. 1989 & 1990 and Weisman et al., Science 249: 146–151 (1990)). Furthermore, co-formulation of the sCR1/pBSCR1c product with p-anisoylated human plasminogen-streptokinase-activator complex (APSAC resulted in similar antihemolytic activity as APSAC alone, indicating that the combination of the complement inhibitor, sCR1, with a thrombolytic agent, could be a useful combination therapy (Fearon et al., Intl. Patent Publication Number W091/05047 published Apr. 18, 1991).

Complement receptor-like proteins are proteins which may be purified by the protocol described herein, such protocol being modified if necessary by routine, non-inventive adjustments that do not entail undue experimentation. Such proteins include allotypes and alleles of CRs, truncated forms, chemically modified forms such as by PEG treatment, and fusion proteins containing a CR moiety. These proteins are referred to as complement receptor-like because they possess or retain sufficient CR protein properties to admit to purification by the process of this invention. Unless specifically identified otherwise, term complement receptor protein also includes complement receptor-like proteins. CR-1-like proteins represent a subset of CR-like proteins including alleles, truncates, chemically modified and fusion proteins derived from the CR-1 allotype. Soluble complement receptor 1 (sCR1), defined herein as a soluble form of human CR1 containing all 30 extracellular SCR domains, is a specific example of a CR-1-like protein.

The complement receptor proteins of this invention can be made by a variety of techniques. If full length native chains are required, then the native molecules may be extracted from the above-identified cell sources. When soluble forms are desired, fragments of the native full length molecules are preferred. Accordingly, DNAs encoding the desired chain fragments, are expressed as recombinantly produced protein fragments. This invention is particularly useful for the purification of sCR1 from conditioned cell culture medium of a variety of sCR1 producing recombinant cell lines. Although one may expect some variation from cell line to cell line and among the various complement receptor products, based on the disclosure herein, it is well within the purview of one of ordinary skill in this art to adapt the invention herein to a particular combination of complement receptor protein and producing cell line.

Generally, genes encoding proteins such as complement receptors may be cloned by incorporating DNA fragments coding for the desired regions of the polypeptide into a recombinant DNA vehicle (e.g., vector) and transforming or transfecting suitable prokaryotic or eukaryotic hosts. Suitable prokaryotic hosts include but are not limited to Escherichia, Streptomyces, Bacillus and the like. Suitable eukaryotic hosts include but are not limited to yeast, such as Saccharomyces and animal cells in culture such as VERO, HeLa, mouse C127, Chinese hamster ovary (CHO), WI-38, BHK, COS, MDCK, and insect cell lines. Particularly preferred host are CHO cell lines deficient in dihydrofolate reductase such as ATCC CRL 1793, CRL 9096 and other cell lines described hereinbelow. Such recombinant techniques have now become well known and are described in *Methods in Enzymology*, (Academic Press) Volumes 65 and 69 (1979), 100 and 101 (1983), and the references cited therein. An extensive technical discussion embodying most commonly used recombinant DNA methodologies can be found in Maniatis, et al. , *Molecular Cloning*, Cold Spring Harbor Laboratory (1982) or *Current Protocols in Molecular Biology*, Greene Publishing (1988,1991).

One way of obtaining a DNA fragment encoding a desired polypeptide such as a complement receptor is via cDNA cloning. In this process, messenger RNA (mRNA) is isolated from cells known or suspected of producing the desired protein. Through a series of enzymatic reactions, the mRNA population of the cells is copied into a complementary DNA (cDNA). The resulting cDNA is then inserted into cloning vehicles and subsequently used to transform a suitable prokaryotic or eukaryotic host. The resulting cDNA "library" is comprised of a population of transformed host cells, each of which contain a single gene or gene fragment. The entire library, in theory, provides a representative sample of the coding information present in the mRNA mixture used as the starting material.

The libraries can be screened using nucleic acid or antibody probes in order to identify specific DNA sequences. Once isolated, these DNA sequences can be modified or can be assembled into complete genes. Alternatively, as described in this invention, specific fragments of a gene can be engineered independently of the rest of the gene. Protein fragments encoded by these engineered gene fragments may not be found in nature, yet they may have significant utility in the treatment of undesirable physiological conditions. The genetic engineering of soluble complement receptor for the prevention and/or treatment of disorders involving complement activity is one such case.

Once the gene or gene fragment has been cloned, the DNA may introduced into an expression vector and that construction used to transform an appropriate host cell. An expression vector is characterized as having expression control sequences as defined herein, such that when a DNA sequence of interest is operably linked thereto, the vector is capable of directing the production of the product encoded by the DNA sequence of interest in a host cell containing the vector. With specific reference to this invention, it is possible to assemble fragments of a single coding sequence such that upon expression a soluble receptor protein is formed. A particularly efficacious application of this protocol to sCR1 recombinant production is found in the Fearon, et al. PCT Applications W089/09220, published Oct. 5, 1989, and W091/05047 published on Apr. 18, 1991, cited above.

After the recombinant product is produced it is desirable to recover the product. If the product is exported by the cell producing it, the product can be recovered directly from the cell culture medium. If the product is retained intracellularly, the cells must be physically disrupted by mechanical, chemical or biological means in order to obtain the intracellular product.

In the case of a protein product, the purification protocol should not only provide a protein product that is essentially free of other proteins, by which is meant at least 80% and preferably greater than 95% pure with respect to total protein in the preparation, but also eliminate or reduce to acceptable levels other host cell contaminants, DNA, RNA, potential pyrogens and the like.

As mentioned above, a variety of host cells may be used for the production of the receptors of this invention. The choice of a particular host cell is well within the purview of the ordinary skilled artisan taking into account, inter alia, the nature of the receptor, its rate of synthesis, its rate of decay and the characteristics of the recombinant vector directing the expression of the receptor. The choice of the host cell expression system dictates to a large extent the nature of the cell culture procedures to be employed. The selection of a particular mode of production be it batch or continuous, spinner or air lift, liquid or immobilized can be made once the expression system has been selected. Accordingly, fluidized bed bioreactors, hollow fiber bioreactors, roller bottle cultures, or stirred tank bioreactors, with or without cell microcarrier may variously be employed. The criteria for such selection are appreciated in the cell culture art. They are not detailed herein because they are outside the scope of this invention. This invention relates to the purification of complement receptors given their existence in a conditioned cell culture medium.

As mentioned above this invention relates, inter alia, to application of hydrophobic interaction chromatography (HIC) to the purification and analysis of complement receptor proteins. Hydrophobic molecules in a aqueous solvent will self-associate. This association is due to hydrophobic interactions. It is now appreciated that macromolecules such as proteins have on their surface extensive hydrophobic patches in addition to the expected hydrophilic groups. HIC is predicated, in part, on the interaction of these patches with hydrophobic ligands attached to chromatographic supports. A hydrophobic ligand coupled to a matrix is variously referred to herein as an HIC support, HIC gel or HIC column. It is further appreciated that the strength of the interaction between the protein and the HIC support is not only a function of the proportion of non-polar to polar surfaces on the protein but by the distribution of the non-polar surfaces as well.

A number of matrices may be employed in the preparation of HIC columns, the most extensively used is agarose. Silica and organic polymer resins may be used. Useful hydrophobic ligands include but are not limited to alkyl groups having from about 2 to about 10 carbon atoms, such as a butyl, propyl, or octyl; or aryl groups such as phenyl. Conventional HIC products for gels and columns may be obtained commercially from suppliers such as Pharmacia LKB AB, Uppsala, Sweden under the product names butyl-SEPHAROSE®, phenyl-SEPHAROSE® CL-4B, octyl-SEPHAROSE® FF and phenyl-SEPHAROSE® FF; Tosoh Corporation, Tokyo, Japan under the product names TOYOPEARL Butyl 650M (Fractogel TSK Butyl-650) or TSK-GEL phenyl-5PW; Miles-Yeda, Rehovot, Israel under the product name alkyl-agarose, wherein the alkyl group contains from 2-10 carbon atoms, and J. T. Baker, Phillipsburg, N.J. under the product name Bakerbond WP-HI-propyl.

It is also possible to prepare the desired HIC column using conventional chemistry. For example, matrix/ligand combinations of the form

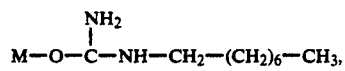

wherein M is matrix such as agarose can be formed after cyanogen bromide activation of the agarose by coupling with an alkylamine as is taught by Er-el, Z. et al. Biochem Biophys. Res. Comm. 49:383 (1972). Alternatively, combinations of the form

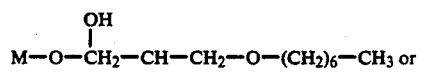

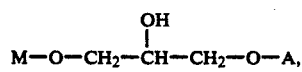

wherein M is a matrix such as agarose and A is aryl, can be prepared by a glycidyl ether coupling procedure(Ulbrich, V. et. al. Coll. Czech. Chem. Commum. 9:1466 (1964)). Briefly, a gel, usually agarose, is transferred to an organic solvent, e.g., dioxane. This is done stepwise (100 ml portions to 100 ml sedimented gel) on a Büchner funnel: (1) one washing with water-dioxane (4:1), (2) one washing with water-dioxane (3:2), (3) one washing with water-dioxane (2:3), (4) one washing with water-dioxane (1:4) and (5) seven washings with dioxane. 100 ml dioxane is added to 100 ml of sedimented gel and 2 ml of a 48% solution of boron trifluoride etherate in diethyl ether is added and stirred for five minutes. 1 ml of the appropriate glycidyl ether dissolved in 10 ml of dioxane is added dropwise from a separatory funnel. The reaction takes about 40 minutes. After the reaction the derivitized gel is transferred back to an aqueous environment but reversing steps (4) to (1) above and finishing with a final wash in water. The amount of ligand to be coupled to the gel can be controlled by varying the amount of glycidyl ether added to the reaction mix. The reaction can be represented generally as follows:

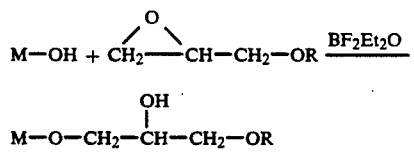

wherein M is a matrix such as agarose and R is alkyl or aryl.

Ligand density is an important parameter in that it influences not only the strength of the interaction but the capacity of the column as well. The ligand density of the commercially available phenyl or octyl phenyl gels is on the order of 40 moles/ml gel bed. Gel capacity is a function of the particular protein in question as well pH, temperature and salt concentration but generally can be expected to fall in the range of 3-20 mg/ml of gel.

The choice of a particular gel can be determined by the skilled artisan. In general the strength of the interaction of the protein and the HIC ligand increases with the chain length of the of the alkyl ligands but ligands having from about 4 to about 8 carbon atoms are suitable for most separations. A phenyl group has about the same hydrophobicity as a pentyl group, although the selectivity can be quite different owing to the possibility of pi-pi interaction with aromatic groups on the protein.

Adsorption of the proteins to a HIC column is favored by high salt concentrations, but the actual concentrations can vary over a wide range depending on the nature of the protein and the particular HIC ligand chosen. Various ions can be arranged in a so-called soluphobic series depending on whether they promote hydrophobic interactions (salting-out effects) or disrupt the structure of water (chaotropic effect) and lead to the weakening of the hydrophobic interaction. Cations are ranked in terms of increasing salting out effect as $Ba^{++} < Ca^{++} < Mg^{++} < Li^+ < Cs^+ < Na^+ < K^+ < Rb^+ < NH_4^+$. While anions may be ranked in terms of increasing chaotropic effect as $PO_4^{---} < SO_4^{--} < CH_3COO^- < Cl^- < Br^- < NO_3^- < ClO_4^- < I^- < SCN^-$. Accordingly, salts may be formulated that influence the strength of the interaction as given by the following relationship:

$$Na_2SO_4 > NaCl > (NH_4)_2SO_4 > NH_4Cl > NaBr > NaSCN$$

In general, salt concentrations of between about 0.75 and about 2M ammonium sulfate or between about 1 and 4M NaCl are useful.

The influence of temperature on HIC separations is not simple, although generally a decrease in temperature decreases the interaction. However, any benefit that would accrue by increasing the temperature must also be weighed against adverse effects such an increase may have on the activity of the protein.

Elution, whether stepwise or in the form of a gradient, can be accomplished in a variety of ways: (a) by changing the salt concentration, (b) by changing the polarity of the solvent or (c) by adding detergents. By decreasing salt concentration adsorbed proteins are eluted in order of increasing hydrophobicity. Changes in polarity may be affected by additions of solvents such as ethylene glycol or (iso)propanol thereby decreasing the strength of the hydrophobic interactions. Detergents function as displacers of proteins and have been used primarily in connection with the purification of membrane proteins.

As mentioned above HIC is particularly useful when used in combination with other protein purification techniques. That is to say it is preferred to apply HIC to material that has been partially purified by other protein purification procedures. By the term "partially purified" is meant a protein preparation in which the protein of interest is present in at least 5 percent by weight, more preferably at least 10% and most preferably at least 45%. Accordingly, the application of HIC is best appreciated in the context of an overall purification protocol for complement receptor proteins. It has been found to be useful, for example, to subject a sample of conditioned cell culture medium to partial purification prior to the application of HIC. By the term "conditioned cell culture medium" is meant a cell culture medium which has supported cell growth and/or cell maintenance and contains secreted product. A concentrated sample of such medium is subjected to one or more protein purification steps prior to the application of a HIC step. The sample may be subjected to ion exchange chromatography as a first step. As mentioned above various anionic or cationic substituents may be attached to matrices in order to form anionic or cationic supports for chromatography. Anionic exchange substituents include diethylaminoethyl(DEAE), quaternary aminoethyl(QAE) and quaternary amine(Q) groups. Cationic exchange substituents include carboxymethyl (CM), sulfoethyl(SE), sulfopropyl(SP), phosphate(P) and sulfonate(S). Cellulosic ion exchange resins such as DE23, DE32, DE52, CM-23, CM-32 and CM-52 are available from Whatman Ltd. Maidstone, Kent, U.K. SEPHADEX ®-based and cross-linked ion exchangers are also known. For example, DEAE—, QAE—, CM—, and SP— SEPHADEX ® and DEAE—, Q—, CM— and S—SEPHAROSE ® are all available from Pharmacia AB. Further both DEAE and CM derivilized ethylene glycol-methacrylate copolymer such as TOYOPEARL DEAE-650S and TOYOPEARL CM-650S are available from Toso Haas Co., Philadelphia, Pa. Because elution from ionic supports usually involves addition of salt and because, as mentioned previously HIC is enhanced under increased salt concentrations, the introduction of a HIC step following an ionic exchange chromatographic step or other salt mediated purification step is particularly preferred. It is preferred that a cationic exchange chromatographic step and an ammonium sulfate precipitation step precede the application of HIC. Additional purification protocols may be added including but not necessarily limited to further ionic exchange chromatography, size exclusion chromatography, viral inactivation, concentration and freeze drying.

When the eluate resulting from HIC is subjected to further ion exchange chromatography, it is preferred that both anionic and cationic procedures be employed.

As mentioned above, gel filtration chromatography affects separation based on the size of molecules. It is in effect a form of molecular sieving. It is desirable that no interaction between the matrix and solute occur, therefore, totally inert matrix materials are preferred. It is also desirable that the matrix be rigid and highly porous. For large scale processes rigidity is most important as that parameter establishes the overall flow rate. Traditional materials e.g. SEPHADEX ® or BIO-GEL ® were sufficiently inert and available in a range of pore sizes, however these gels were relatively soft and not particularly well suited for large scale purification. More recently, gels of increased rigidity have been developed (e.g. SEPHACRYL ®, UTROGEL ®, FRACTOGEL ® and SUPEROSE ®). All of these materials are available in particle sizes which are smaller than those available in traditional supports so that resolution is retained even at higher flow rates. TOYOPEARL HW series matrices (Toso Haas) are preferred.

For purposes of illustration only, this invention was applied to the purification of a complement receptor of the soluble type. More specifically, to a soluble CR1 construct containing leader, LHR-A, LHR-B, LHR-C, LHR-D, SCR29, SCR30 regions up to and including the first alanine residue of the transmembrane region; and corresponding to the CR1 encoding sequences in plasmid pBSCR1c of Fearon et al., 1989, Intl. Patent Publication Number WO89/09220, published Oct. 5, 1989 (hereinafter "TP10HD"). The construction of a recombinant system for the production of TP10HD is detailed in the above mentioned PCT Application and summarized as follows.

CHO cells were trypsinized and plated out a $5\times10^5$ per 60mm dish and left in the growth medium (Hams F12 nutrient medium (041-1765) with 1% stock glutamine (043-05030), 1% stock pen/strep (043-05070) and 10% bovine fetal calf serum (011-6290),Gibco, Paisley, Scotland) at 37° C. in a humidified incubator in an atmosphere of 5% $CO_2$/95% air. After 21 hours the cells were used for DNA transfection. An expression plasmid containing the sCR1 coding sequence from pBSCR1c was co-transfected with pSV2dhfr into a dhfr-requiring Chinese Hamster Ovary cell line (CHO-DUXBII). The transfection was carried in growth medium and employed the calcium coprecipitation/ glycerol shock procedure as described in:DNA Cloning, D. M. Glover ed. (Chap. 15, C. Gorman). Following transfection with pBSCR1c/pTCSgpt and pSV2dhfr, the cells were maintained in growth medium for 46 hours under growth conditions (as described above) prior to the selection procedure.

The selection and co-amplification procedure was carried out essentially as described by R. J. Kaufman, et al. ( Mol. Cell. Biol. 5:1750–1759 (1985)). Forty-six hours post transfection the cells were changed to selective medium MEM ALPHA (041-02571), 1% stock glutamine, 1% stock pen/strep (043-05070) and dialysed bovine fetal calf serum (220-6300AJ) (Gibco, Paisley, Scotland). The cells were maintained in the selective medium for 8–10 days until dhfr+ colonies appeared. When the colonies were established the cells were changed into a selective medium containing methotrexate, (A6770, Sigma Chem. Co., St. Louis, Mo.). The methotrexate concentration was initially 0.02 $\mu$M and was increased stepwise to 5 $\mu$M. During the amplification procedure aliquots of growth medium from growing cells were assayed for TP10HD production by ELISA. Any complement receptor secreting recombinant cell line (e.g. ATCC CRL 10052) may be used to supply the conditioned medium for purification according to this invention, but a particular cell line certainly is not required.

A transfected CHO cell line capable of producing TP10HD can be cultured by a variety of cell culture techniques. For the application of this invention the particular method of culturing is not critical, however for purposes of illustration, one method for cell culturing which may be used is a continuous perfusion process predicated on the Verax fluidized bed technology as embodied in U.S. Pat. Nos. 4,861,714; 4,863,856; 4,978,616 and 4,997,753, the contents of which are incorporated by reference. Accordingly, transfected cells such as those described above, are scaled up in CCM-3 medium (a mixture of DMEM, Ham's F-12, bovine serum albumin and other nutrient supplements) supplemented with 10% fetal bovine serum (FBS) and 5mM methotrexate (MTX). The cell population was expanded in roller bottles until sufficient numbers of cells were available for inoculating a bioreactor. Prior to inoculation a S200 bioreactor underwent clean-in-place (CIP) and steam-in-place (SIP) cycles. It was then filled with CCM-3 medium containing 5% FBS and charged with 450 grams of microspheres. The microspheres were conditioned with medium prior to inoculation. The reactor was inoculated with cells and the operating parameters were: pH 7.2., 37° C., inlet (bottom of fluidized bed) dissolved $O_2$ between 100 and 400 torr, exit (top of fluidized bed) dissolved $O_2$ between 0 and 200 torr. Following an initial batch phase, medium perfusion was initiated, with periodic increases in rate so as to maintain the glucose concentration at 1.0 g/L. This was continued until a sufficient number of cells had accumulated in the reactor to inoculate a S2000 bioreactor. Following CIP and SIP, a S-2000 reactor was filled with CCM-3 medium supplemented with 5% FBS and 5 mM MTX and charged with 5000 grams of microspheres. These microspheres were conditioned with medium prior to inoculation. The operating conditions in respect of temperature, reactor arrangement and dissolved $O_2$ are as given above. The microspheres from the S-200 reactor were aseptically transferred into the S-2000 reactor to initiate batch phase. When the glucose concentration fell below 1.5 g/L, the growth phase was started by initiating medium perfusion (CCM-3, 5% FBS and 5 mM MTX) at a rate sufficient to maintain the glucose concentration at 1.0 g/L. Cell growth was monitored on-line by measuring oxygen uptake and glucose consumption rates. When a sufficient number of cells had accumulated within the reactor, the perfusion medium was changed to CCM-3 supplemented with 1% FBS and 5mM MTX, transition medium. Again this perfusion rate was modified so as to maintain a glucose concentration of 1.0 g/L. Following further growth in the transition medium, the perfusion medium was changed once again to the production medium, CCM-3 supplemented with 5 mM MTX. The perfusion rate was increased to maintain a glucose concentration of 1.0 g/L. Thereafter, either exit dissolved $O_2$ or recycle flow rate setpoints were lowered to maintain control over the reactor. The production phase typically lasts for about 60 days.

Between 400 and 1600 liters of reactor permeate, stored a 4–8° C., were processed through a Millipore Prostak Microfiltration Unit. The cell-free permeate from this operation supplied the ultrafiltration step. The permeate was concentrated 30–60$\times$ with a Millipore Spiral Wound System. Following concentration, the retentate was drained into a holding tank and the system was filled with 5–20 L of 50 mM phosphate buffer, pH 7.5. The wash buffer was drained from the system and combined with the retentate. The ultrafiltration concentrate was filtered through a prefilter and a terminal 0.22 mm filter into a previously autoclaved Nalgene bottle. Nominally 800 ml of concentrate are dispersed into each bottle and stored frozen.

As mentioned previously, the particular recombinant production system and the particular cell culturing protocol is outside the scope of this invention. The system and protocol discussed above are representative of the many options available to the skilled artisan and they are included herein for purposes of illustration only. The purification protocol which is the subject of this invention is applicable, with only routine modification, to a variety of recombinant complement receptor and receptor-like proteins regardless of how they are produced or cultured.

The purified complement receptor proteins obtained by practicing the process of this invention have the following properties: 1) greater than 95% CR protein by weight; 2) stable to proteolytic degradation at 4° C. for at least three months; 3) low (<1 E.U./mg protein) endotoxin; 4) low (<1 pg/mg protein) DNA; 5) non-CR protein <5% by weight; and 6) virally inactive. The following examples further illustrate this invention but are not offered by way of limitation of the claims herein.

EXAMPLE I

INTRODUCTION

The procedure outlined below was developed for the isolation and purification of soluble complement receptor-1 (sCR1) from conditioned cell culture medium concentrate. This process is designed to prepare sCR1 of >95% protein purity while removing impurities derived from the host cell, cell culture medium, or other raw materials. The recovery procedure consists of nine steps including cation and anion exchange, hydrophobic interaction, and size exclusion chromatography; an ammonium sulfate precipitation; and two viral inactivation treatments. Each step is described in detail below. Steps 1 through 5 are carried out at 2-8° C., and steps 6 through 9 are performed at 20-25° C.

STEP 1: MEDIA PRETREATMENT

While stirring, conditioned media concentrate is adjusted to pH 5.2 by the addition of 1 N HCl. When the addition is complete, stirring is continued and the pH monitored for 10 min. The pH adjustment produces a heavy precipitate. Clarification is achieved by microfiltration through a series of 3 Millipore Polygard-CR filters connected in tandem (5 micron to 0.5 micron to 0.1 micron). The sCR1 is recovered in the filtrate.

The acidification and filtration of the medium concentrate removes both non-sCR1 protein and non-proteinaceous material; and adjusts the sCR1 containing filtrate to the appropriate pH for subsequent S SEPHAROSE chromatography

STEP 2: PHARMACIA S SEPHAROSE FAST FLOW CHROMATOGRAPHY

The pH 5.2 filtrate is loaded onto a column of Pharmacia S SEPHAROSE Fast Flow gel previously equilibrated with Buffer A, at a flow rate of 60 cm/hr, and a capacity of <3 gram sCR1/L bed volume. The column is washed at 150 cm/hr with 3 to 5 bed volumes of Buffer A, followed by 5 to 10 bed volumes of Buffer B. The sCR1 binds to the column and is eluted with Buffer C. The column is stripped by washing with 3 bed volumes of Buffer D.

The S SEPHAROSE chromatography removes a large proportion of cell and media derived impurities (particularly protein) and concentrates sCR1 in the Buffer C column eluate for further processing.

STEP 3: AMMONIUM SULFATE PRECIPITATION

The S SEPHAROSE Buffer C eluate is adjusted to 1.2 M ammonium sulfate by the addition of Buffer E. When the addition is complete, stirring is stopped, and the mixture is allowed to stand overnight.

The precipitate containing sCR1 is collected by centrifugation for 10 min at 8000×G.

The pelleted material is resuspended by gentle stirring in approximately 4 L of Buffer F. Additional Buffer F is added until the absorbance of the solution at 280 nm is 1.5 O.D. units. The solution is stirred overnight, and filtered through a Millipore Polygard-CR 0.1 micron filter.

The ammonium sulfate precipitation removes additional impurities, and prepares the sCR1 for hydrophobic interaction chromatography.

STEP 4: TOYOPEARL BUTYL-650M CHROMATOGRAPHY

The resolubilized and filtered ammonium sulfate pellet is adjusted to 0.8 M ammonium sulfate by addition of Buffer E while stirring.

When addition is complete, the mixture is loaded onto a column of TOYOPEARL Butyl-650 M gel previously equilibrated with Buffer G, at a flow rate of 150 cm/hr, and capacity of ≦4 gram total protein/L column volume. The buffers and column are maintained at 2-8° C. When loading is completed the column is washed with 2-3 bed volumes of Buffer G, washed with 3 bed volumes of Buffer H, and the bound sCR1 eluted with Buffer I.

STEP 5: VIRAL INACTIVATION AND PHARMACIA SEPHADEX G 25 CHROMATOGRAPHY

Solid GuHCl is added to the Butyl Buffer I eluate to a concentration of approximately 2 M and stirred until completely dissolved. The pH is monitored and if necessary adjusted to pH 7.0 using 2.5 N NaOH.

When the GuHCl is completely dissolved, the solution is held for 6 minutes and loaded onto a column of Pharmacia SEPHADEX G25, previously equilibrated with Buffer J, at a flow rate of 60 cm/hr. The volume of the load should not exceed 25% of the SEPHADEX G25 column volume.

After the sCR1 is eluted (elutes in the void volume), the column is washed with Buffer J until the "salt" peak is eluted and the conductivity has returned to baseline level. The SEPHADEX G25 product is adjusted to pH 11 by addition of 2.5 M NaOH, the solution is held at pH 11 for 16 minutes, and readjusted to pH 9.0 using 2.5 M HCl. The material is now ready for anion exchange chromatography.

The GuHCl and pH 11 treatments afford retroviral inactivation, if any virus is present, and the SEPHADEX G25 chromatography prepares the sCR1 product for DEAE TOYOPEARL chromatography.

STEP 6: TOYOPEARL DEAE-650S CHROMATOGRAPHY

The SEPHADEX G25 product is loaded onto a column of TOYOPEARL DEAE-650S gel, previously equilibrated with Buffer J, at a flow rate of 150 cm/hr and capacity of ≦6 gram protein/L column volume. After loading the column is washed with 3 column bed volumes of Buffer J. The bound sCR1 is eluted with a 5 column volume linear gradient starting from 100% Buffer J and extending to 100% Buffer K. The column is stripped by washing with 3 bed volumes of Buffer L.

The TOYOPEARL DEAE chromatography removes contaminant proteins, DNA, and potential viral impurities.

STEP 7: TOYOPEARL CM-650S CHROMATOGRAPHY

Dilute the DEAE product with 2 volumes of Buffer M and adjust to pH 5.5 with 2.5 N HCl. Load the diluted mixture onto a column of TOYOPEARL CM-650S gel, previously equilibrated with Buffer M, at a flow rate of 150 cm/hr, and capacity of ≦11 gram protein/L column volume. After the load is complete, wash with 3 column bed volumes of Buffer M and elute the bound sCR1 with a 5 column volume linear gradient extending from 100% Buffer M to 100% Buffer N. The column is stripped with 3 bed volumes of Buffer O. The product containing eluate is neutralized with 1/10 volume of 0.5 M dibasic sodium phosphate, and is now ready for size exclusion chromatography.

The TOYOPEARL CM chromatography removes contaminant proteins, DNA, and potential viral impurities.

STEP 8: TOYOPEARL HW65S

CHROMATOGRAPHY

The TOYOPEARL CM product is loaded onto a column of TOYOPEARL HW65S, previously equilibrated with Buffer F, at a flow rate of 30 cm/hr. The volume of the load should not exceed 5% of the total TOYOPEARL HW65S column volume. Collect the entire product peak until the absorbance decreases to 10% of the maximum absorbance. The material is now ready for final concentration.

The size exclusion chromatography removes the last traces of low molecular weight protein impurities, and serves to buffer exchange the sCR1 into the final target buffer.

STEP 9: CONCENTRATION AND FINAL FILTRATION

The TOYOPEARL HW65S pool is concentrated to 5-6 mg/ml using a Pharmacia Minisette Ultrafiltration unit fitted with a 100 K MWCO Omega membrane. The concentrated product is filtered through a Millipore 0.2 micron Millipak filter

| BUFFERS | |
|---|---|
| Buffer A | 20 mM sodium phosphate, 60 mM NaCl, pH 5.2 |
| Buffer B | 20 mM sodium phosphate, 100 mM NaCl, pH 6.0 |
| Buffer C | 20 mM sodium phosphate, 500 mM NaCl, pH 7.0 |
| Buffer D | 1 M NaCl |
| Buffer E | 3 M ammonium sulfate, 100 mM sodium phosphate, pH 7.0 |
| Buffer F | 10 mM sodium phosphate, 0.9% w/v NaCl, pH7 |
| Buffer G | 0.8 M ammonium sulfate, 100 mM sodium phosphate, pH 7.0 |
| Buffer H | 0.7 M ammonium sulfate, 100 mM sodium phosphate, pH 7.0 |
| Buffer I | 0.09 M ammonium sulfate, 100 mM sodium phosphate, pH 7.0 |
| Buffer J | 50 mM Tris/Tris.HCl, pH 9.0 |
| Buffer K | 50 mM Tris/Tris.HCl, 0.2 M NaCl, pH 9.0 |
| Buffer L | 50 mM Tris/Tris.HCl, 1.0 M NaCl, pH 9.0 |
| Buffer M | 50 mM MES/MES.Na, pH 5.5 |
| Buffer N | 50 mM MES/MES.Na, 0.25 M NaCl, pH 5.5 |
| Buffer O | 50 mM MES/MES.Na, 1.0 M NaCl, pH 5.5 |

TABLE I

PURIFICATION SUMMARY

| STEP | CONCENTRATION PROTEIN[a] | CONCENTRATION sCR-1[b] | TOTAL PROTEIN | TOTAL sCR-1 | TOTAL STEP[b] | YIELD CUMULATIVE[b] | ENDOTOXIN (EU/mg sCR-1) |
|---|---|---|---|---|---|---|---|
| 50x Conc Media | 6.60 | 0.453 | 604 | 41.5 | 100 | 100 | 13 |
| Filtrate | 5.44 | 0.387 | 564 | 40.1 | 97 | 97 | 15 |
| S Sepharose Ammonium Sulfate/ | 3.44 | 1.54 | 80.1 | 35.6 | 89 | 86 | 0.78 |
| Butyl 650S | 0.76 | 0.686 | 31.6 | 28.5 | 80 | 69 | 0.17 |
| Sephadex G-25 | 0.50 | 0.471 | 29.9 | 28.4 | 100 | 68 | 0.13 |
| DEAE 650S | 3.19 | 2.93 | 29.0 | 26.7 | 94 | 64 | 0.01 |
| CM 650S | 4.10 | 3.77 | 27.7 | 25.4 | 95 | 61 | 0.01 |
| HW65 Product | 1.27 | 1.24 | 25.2 | 24.6 | 97 | 59 | 0.10 |
| Final Product | 5.53[c] | 5.29 | 25.1 | 24.0 | 98 | 58 | 0.02 |

[a] by Absorbance at 280 nm, $a_s = 1.17$ mL mg$^{-1}$ cm$^{-1}$; $\epsilon_{280} = 2.53 \times 10^5$ M$^{-1}$ cm$^{-1}$
[b] by Elisa
[c] by amino acid analysis

What is claimed is:

1. A method for purifying a complement receptor protein from a mixture containing same comprising sequentially contacting said mixture with a cationic chromatographic support, a hydrophobic interaction chromatographic support, a size exclusion chromatographic support and selectively eluting the protein from each support.

2. The method according to claim 1 wherein the receptor is selected from the group consisting of CR1, CR2, CR3 and CR4.

3. The method according to claim 2 wherein the receptor is CR1 and fragments thereof.

4. The method according to claim 3 wherein the receptor is a soluble fragment of CR1.

5. The method according to claim 4 wherein the receptor is TP10HD.

6. The method according to claim 4 for purifying TP10HD from a partially purified mixture containing same comprising loading said mixture onto a butyl-ethylene glycol-methacrylate copolymer column equilibrated with 0.8 M (NH$_4$)$_2$SO$_4$ in 100 mM sodium phosphate, pH 7.0, eluting TP10HD with a 100 mM sodium phosphate buffer, pH 7.0 containing 0.09 M (NH$_4$)$_2$SO$_4$, and washing the column with equilibration buffer followed by washing with 0.7 M(NH$_4$)$_2$SO$_4$ in 100 mM sodium phosphate, pH 7.0 collecting the eluant as column fractions.

7. The method according to claim 6 wherein the further step of pooling the collected fractions containing TP10HD.

8. The method according to claim 1 wherein the cationic chromatographic support is selected from the group consisting of CM- cellulose; CM-and SP- cross-linked dextrans, CM- and S-spherical agarose beads, and CM-ethylene glycol-methacrylate copolymer and elution is by addition of a buffered salt solution.

9. The method according to claim 8 wherein the support S-spherical agarose beads and the salt is NaCl.

10. The method according to claim 8 wherein the salt solution is 20 mM sodium phosphate, 500 mM NaCl, pH 7.0.

11. The method according to claim 1 wherein the HIC support is selected from the group consisting of alkyl$_{C2-C8}$ agarose, aryl-agarose, alkyl-silica, alkyl organic polymer resin.

12. The method according to claim 11 wherein the support is selected from the group consisting of butyl-, phenyl-, and octyl-spherical agarose beads and butyl-, phenyl- and ether-ethylene glycol-methacrylate copolymer.

13. The method according to claim 12 wherein the support is butyl-ethylene glycol-methacrylate copolymer.

14. The method according to claim 1 wherein the HIC support is butyl-ethylene glycol-methacrylate copolymer and the protein is selectively eluted with a low salt buffer.

15. The method according to claim 14 wherein the eluting salt is ammonium sulfate and the buffer is sodium phosphate, pH 7.

16. The method according to claim 15 wherein the protein is selectively eluted with a 100 mM sodium phosphate buffer, pH 7.0 containing 0.09 M ammonium sulfate.

17. The method according to claim 1 wherein the size exclusion chromotographic support is an ethylene glycol-methacrylate copolymer.

18. The method according to claim 17 wherein the support is an ethylene glycol-methacrylate copolymer and elution is with 10 mM sodium phosphate, 0.9% w/v NaCl, pH7.

19. The method for the purification of a complement receptor protein from conditioned cell culture medium containing same comprising sequentially subjecting the medium to (a) a first cationic exchange chromatography, (b) ammonium sulfate precipitation, (c) hydrophobic interaction chromatography, (d) anionic exchange chromatography, (e) a second cationic chromatography and (f) size exclusion chromatography.

20. The method according to claim 19 wherein the first cationic exchange chromatography employs a support selected from the group consisting of CM-cellulose; CM-and SP-cross-linked dextrans, CM- and S-spherical agarose beads and CM-ethylene glycol-methacrylate copolymer and elution is by a buffered salt solution.

21. The method according to claim 20 wherein the support is S-spherical agarose beads and the salt is NaCl.

22. The method according to claim 20 wherein the salt solution is sodium phosphate, 500 mM, NaCl pH 7.0.

23. The method according to claim 19 wherein the ammonium sulfate is present at a concentration of 1.2 M.

24. The method according to claim 19 wherein the hydrophobic interaction chromatographic support is selected from the group consisting of alkyl$_{C2-C8}$-agarose, aryl-agarose, alkyl-silica, alkyl-organic polymer resin.

25. The method according to claim 24 wherein the support is selected from the group consisting of butyl-, phenyl- and octyl-spherical agarose beads and butyl-, phenyl- and ether-ethylene glycol-methacrylate copolymer.

26. The method according to claim 25 wherein the support is butyl-ethylene glycol-methacrylate copolymer.

27. The method according to claim 19 wherein the support is butyl-ethylene glycol-methacrylate copolymer and the protein is selectively eluted with a low salt buffer.

28. The method according to claim 27 wherein the eluting salt is ammonium sulfate and the buffer is sodium phosphate, pH 7.

29. The method according to claim 28 wherein the protein is selectively eluted with a buffer containing 100 mM sodium phosphate, pH 7.0 containing 0.09 mM ammonium sulfate.

30. The method according to claim 19 wherein said anionic exchange chromatography employs a support selected from the group consisting of DEAE-cellulose, DEAE-, QAE-cross-linked dextrans, DEAE-, Q-spherical agarose beads and ethylene glycol-methacrylate copolymer-DEAE.

31. The method according to claim 30 wherein said support is ethylene glycol-methacrylate copolymer-DEAE.

32. The method according to claim 19 wherein said second cationic exchange chromatography employs as a support ethylene glycol-methacrylate copolymer-CM.

33. The method according to claim 19 wherein the size exclusion chromotography employs an ethylene glycol-methacrylate copolymer support.

34. The method according to claim 33 wherein the support is ethylene glycol-methacrylate copolymer.

35. A method for purifying a complement receptor protein from a conditioned cell medium comprising:
(a) concentrating the conditioned cell medium;
(b) absorbing the complement receptor protein onto a cationic chromatographic support;
(c) washing the adsorbed protein with at least one buffer;
(d) eluting the washed protein;
(e) precipitating the protein with ammonium sulfate;
(f) resolubilizing the precipitated protein
(g) adsorbing the solubilized protein from step (f) onto a hydrophobic interaction chromatographic support;
(h) selectively eluting the protein;
(i) adsorbing the eluate of step (h) onto an anionic exchange support;
(j) eluting the adsorbed protein;
(k) adsorbing the eluate from step (j) onto a cationic exchange support;
(l) eluting the adsorbed protein;
(m) subjecting the eluate from step (l) to size exclusion chromatography and
(n) recovering the protein therefrom.

36. The method according to claim 35 which includes the optional step of inactivating viruses if present.

37. The method according to claim 36 wherein the said viral inactivation step is performed after step (h) and before step (i).

38. The method according to claim 37 wherein said viral inactivation step comprises treatment of the eluate with base and with guanidine hydrochloride.

39. The method according to claim 35 wherein the cationic exchange support of step (b) is sulfonate-substituted spherical-agarose beads.

40. The method according to claim 35 wherein the eluate from step (d) is adjusted to 1.2 M ammonium sulfate.

41. The method according to claim 35 wherein the cationic exchange support of step (k) is selected from the group consisting carboxymethyl, sulfoethyl, sulfopropyl, and phosphate substituted cellulosic resins, cross-linked dextrans, spherical agarose beads, and ethylene glycol-methacrylate copolymer.

42. The method according to claim 41 wherein the cationic support is ethylene glycol-methacrylate copolymer-CM.

43. The method according to claim 35 wherein the anionic exchange support is selected from the group consisting of diethylaminoethyl, quaternary aminoethyl and quaternary amine substituted cellulosic resins, cross-linked dextrans, spherical agarose beads or ethylene glycol-methacrylate copolymer.

44. The method according to claim 43 wherein the anionic exchange support is diethylaminoethyl-substituted ethylene glycol-methacrylate copolymer.

45. The method according to claim 35 wherein the hydrophobic interaction chromatographic support is selected from the group consisting of alkyl $C_2$-$C_8$-agarose, aryl-agarose, alkyl-silica, alkyl-organic polymer resin.

46. The method according to claim 45 wherein the support is selected from the group consisting of butyl-, phenyl- and octyl-spherical agarose beads and phenyl-, ether- and butyl-ethylene glycol-methacrylate copolymer.

47. The method according to claim 46 wherein the support is butyl-ethylene glycol-methacrylate copolymer.

48. The method according to claim 35 wherein the size exclusion chromatography employs ethylene glycol-methacrylate copolymer.

49. The method to claim 35 wherein said protein is recovered by pooling and concentrating the protein containing fractions from chromatography step (m) by ultrafiltration.